United States Patent
Banno

Patent Number: 5,831,169
Date of Patent: Nov. 3, 1998

[54] DEVICE FOR MEASURING A DISTANCE BETWEEN A PANEL AND A SHADOW MASK OF A COLOR CRT

[75] Inventor: Tsutomu Banno, Ohtsu, Japan

[73] Assignee: NEC Corporation, Tokyo, Japan

[21] Appl. No.: 806,473

[22] Filed: Feb. 26, 1997

[30] Foreign Application Priority Data

Feb. 28, 1996 [JP] Japan ..................................... 8-040997

[51] Int. Cl.⁶ ............................. G01N 29/00; B23P 19/04
[52] U.S. Cl. ................................ 73/629; 445/30; 445/64; 445/68; 73/628
[58] Field of Search ............................. 73/597, 627, 628, 73/629, 624, 625; 445/64, 30, 63, 66, 67, 68

[56] References Cited

U.S. PATENT DOCUMENTS

| | | | |
|---|---|---|---|
| 3,653,112 | 4/1972 | Smith et al. | 445/68 |
| 4,056,970 | 11/1977 | Sollish | 73/629 |
| 4,175,441 | 11/1979 | Urbanek et al. | 73/599 |
| 4,606,015 | 8/1986 | Yamaguchi | 367/95 |
| 4,979,920 | 12/1990 | Nierenberg | 445/64 |

FOREIGN PATENT DOCUMENTS

| | | |
|---|---|---|
| 58-135547 | 8/1983 | Japan . |
| 60-221930 | 11/1985 | Japan . |

*Primary Examiner*—Hezron E. Williams
*Assistant Examiner*—Rose M. Miller
*Attorney, Agent, or Firm*—Sughrue, Mion, Zinn, Macpeak & Seas, PLLC

[57] ABSTRACT

A device for measuring a distance between a panel and a shadow mask included in a color CRT (Cathode Ray Tube) of the present invention includes a range finder having an emitter for emitting an ultrasonic pulse, and a receiver for receiving it. The emitter emits the ultrasonic pulse toward the inner surface of the panel on which the shadow mask is mounted. The distance or so-called Q value is measured on the basis of a lag between the time when a first reflection from the shadow mask reaches the receiver and the time when a second reflection from the inner surface of the panel reaches the receiver. The device is capable of measuring the Q value without resorting to the removal of the shadow mask, and measuring Q values even smaller than 5 mm without contacting the shadow mask. In addition, the device is easy to handle and small size.

6 Claims, 4 Drawing Sheets

DEVICE FOR MEASURING A DISTANCE BETWEEN A PANEL AND A SHADOW MASK OF A COLOR CRT

BACKGROUND OF THE INVENTION

The present invention relates to a CRT (Cathode Ray Tube) including a shadow mask and, more particularly, to a device for measuring a distance between the inner surface of a panel and that of a shadow mask included in a CRT, i.e., a so-called Q value.

A color CRT with a shadow mask is taught in, e.g., Japanese Patent Laid-Open Publication No. 60-221930. In the color CRT, the distance between the inner surface of a panel and that of the shadow mask, i.e., a Q value, is an essential dimension when a tricolor fluorescent layer or when an electron beam is selectively transmitted through the shadow mask and panel for displaying a picture. To confine the Q value in a preselected range, a measuring device, e.g., a micrometer, has customarily been used to determine whether or not the Q value lies within the preselected range, prior to the assemblage of the CRT. When, this kind of measuring device is used, however, a head included in the device cannot be positioned between the panel and the shadow mask unless the shawdow mask is dismounted from the panel and again mounted to the panel. Such a Q value measuring procedure is time- and labor-consuming.

Another problem with the air micrometer scheme is that the head is about 5 mm thick and cannot measure Q values smaller than 5 mm inclusive. Further, the shadow mask is implemented as a sheet of metal as thin as about 0.1 mm to about 0.2 mm, and therefore easy to deform. Positioning the head on such a thin shadow mask is not desirable.

Japanese Patent Laid-Open Publication No. 58-135547 discloses a measuring device capable of measuring a Q value without resorting to the removal of the shadow mask from the panel. However, this kind of device is bulky and difficult to operate. Moreover, the accuracy of the device is difficult to maintain when the device is included in a production line.

SUMMARY OF THE INVENTION

It is therefore an object of the present invention to provide an easy-to-operate and miniature device capable of measuring a distance between a panel and a shadow mask included in a CRT without resorting to the removal of the mask or contacting the mask, and even when the distance or Q value is smaller than 5 mm inclusive.

In accordance with the present invention, in a range finder device for measuring a distance between the inner surface of a panel and that of a shadow mask mounted inside of the panel, the range finder is positioned inside of the panel and shadow mask, and measures a distance of the inner surface of the panel and that of the inner surface of the shadow mask without contacting the panel or the shadow mask.

BRIEF DESCRIPTION OF THE DRAWINGS

The above and other objects, features and advantages of the present invention will become apparent from the following detailed description taken with the accompanying drawings in which.

In the drawings, identical reference numerals denote identical structural elements.

DESCRIPTION OF THE PREFERRED EMBODIMENTS

Figure 1:
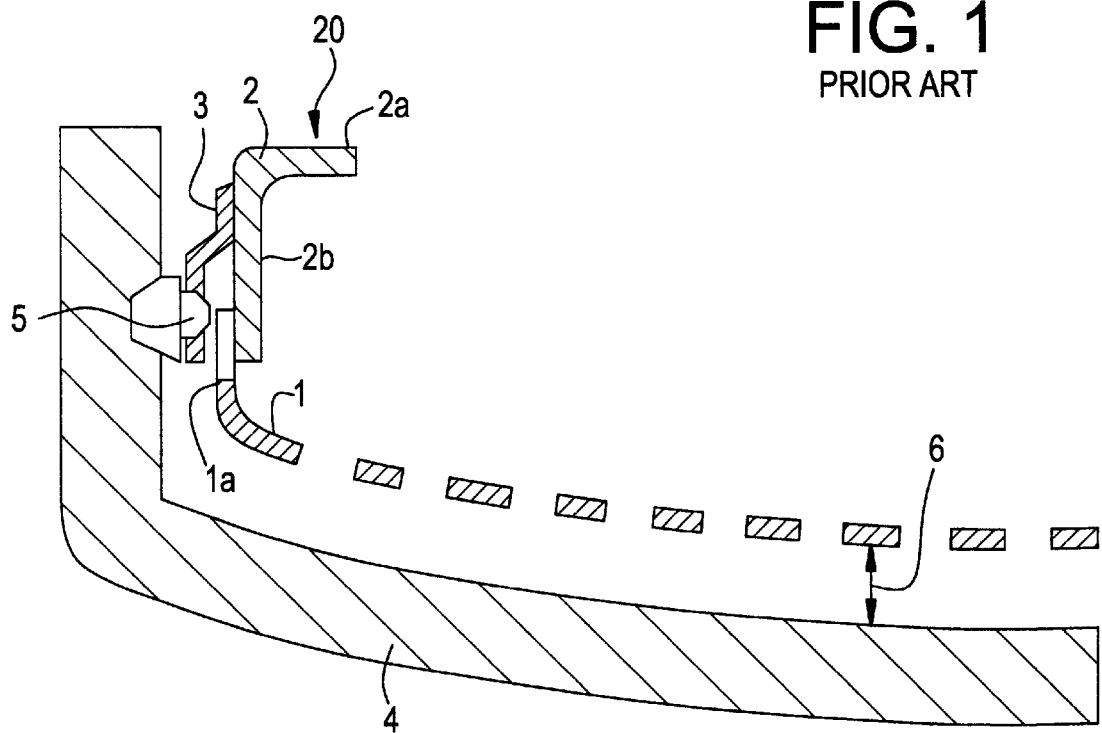
FIG. 1 is a section showing a positional relation between a panel and a shadow mask included in a conventional color CRT.

To better understand the present invention, brief reference will be made to a conventional color CRT, shown in FIG. 1. The CRT to be described is taught in Japanese Patent Laid-Open Publication No. 60-221930 mentioned earlier. As shown, the CRT includes a shadow mask 1 having a skirt portion 1a contiguous with the peripheral portion of the mask 1. A frame 2 has a substantially rectangular frame-like flange 2a and a side wall 2b perpendicular to the flange 2a. A panel 4 has a panel pin 5 studded on its inner surface. A spring 3 is affixed to the side wall 2b of the frame 2. The skirt portion 1a of the shadow mask 1 is welded to the side wall 2b of the frame 2, constituting a shadow mask assembly 20. The assembly 20 is mounted on the panel 4 via the spring 3 and panel pin 5.

Figure 2:
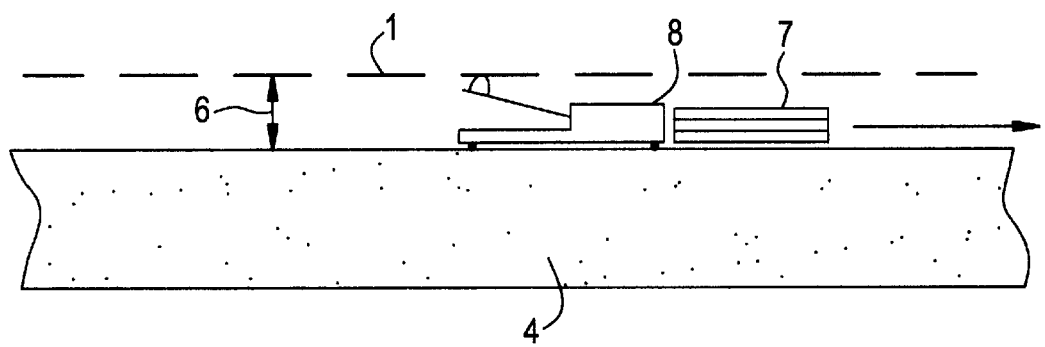
FIG. 2 shows a positional relation between the panel and shadow mask shown in FIG. 1 and a conventional device for measuring a distance between the panel and the shadow mask.

The inner surface of the panel 4 and the shadow mask 1 are spaced by a distance 6 generally referred to as a Q value. The distance 6 must be confined in a preselected range, as stated earlier. It has been customary to determine whether or not the shadow mask assembly 20 has been constructed as designed, i.e., whether or not the Q value lies in the preselected range by using an air micrometer, before assembling the CRT. As shown in FIG. 2, the air micrometer, not shown, has a measuring head 8 disposed between the shadow mask 1 and the inner surface of the panel 4 so as to measure the distance or Q value 6. The head 8 is connected to the air micrometer by a vinyl pipe 7. A change in the air pressure of the head 8 is transmitted to the air micrometer by the vinyl pipe 7.

However, a problem with the air micrometer scheme is that the head 8 cannot be positioned between the panel 4 and the shadow mask 1 unless the mask 1 is dismounted from the panel 4 and again mounted to the panel 4. Specifically, after the shadow mask 1 has been removed from the panel 4, the head 8 is located at a preselected position on the panel 4. Then, the shadow mask 1 is again mounted to the panel 4. After the Q value has been measured by the head 8, the shadow mask 1 is again removed from the panel 4 in order to remove the head 8. Finally, the shadow mask 1 is again mounted to the panel 4. Such a procedure is time- and labor-consuming.

Another problem with the air micrometer scheme is that the head 8 is about 5 mm thick and cannot measure Q values smaller than 5 mm inclusive. Particularly, a color CRT for display whose shadow mask 1 has a small aperture pitch has a small Q value. It is therefore necessary to measure Q values even smaller than 5 mm. Further, the shadow mask 1 is implemented as a sheet of metal as thin as about 0.1 mm to about 0.2 mm, and therefore easy to deform. Positioning the head 8 on such a thin shadow mask 1 is not desirable.

Figure 3:
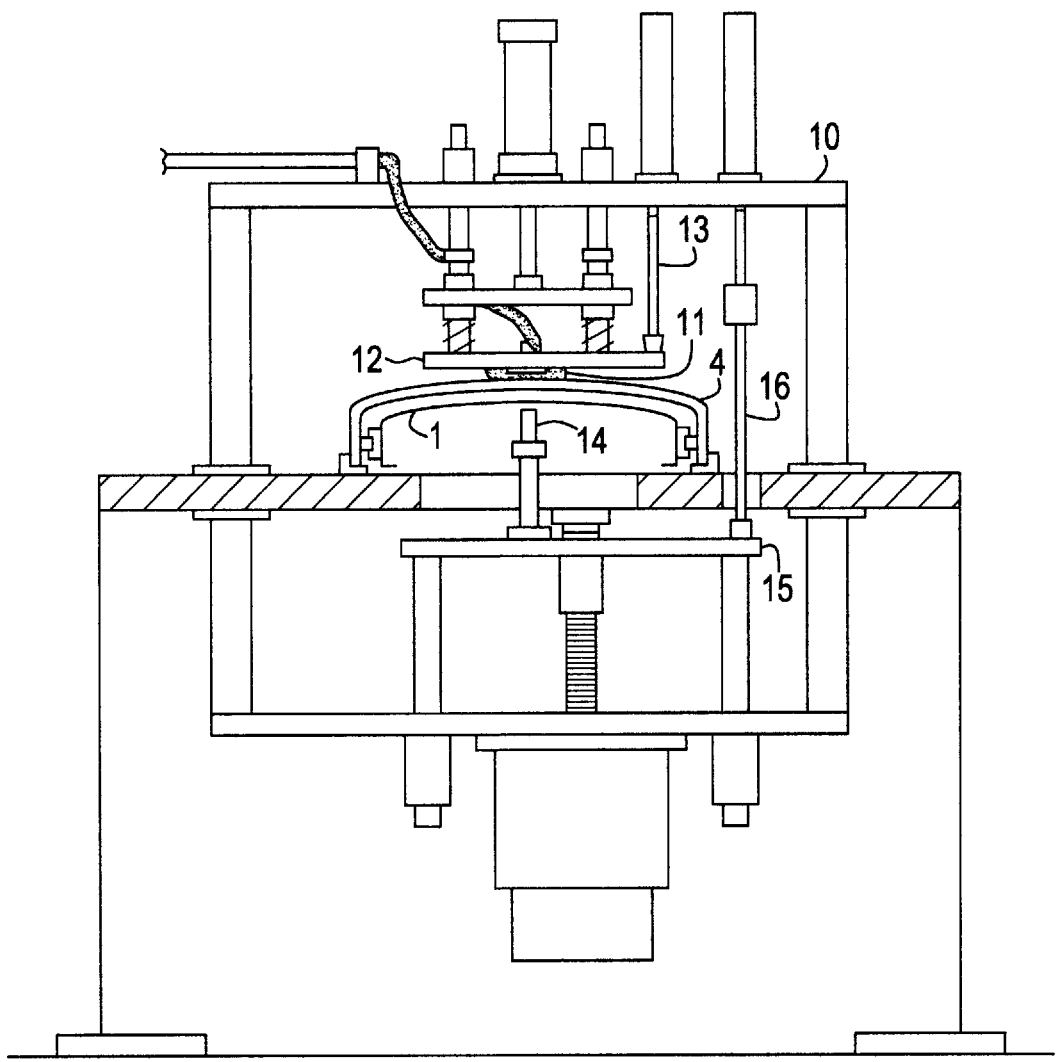
FIG. 3 shows another conventional device measuring the distance.

FIG. 3 shows another conventional measuring device so constructed as to solve the above problems and disclosed in Japanese Patent Laid-Open Publication No. 58-135547 also mentioned earlier. As shown, the device measures the thickness of the panel 4 with an ultrasonic wave system, and measures the position of the shadow mask 1 with an eddy current system. Further, the device uses a linear scale 13 to measure the position of a stage 12 on which an ultrasonic range finder 11 is mounted, and measures the position of a stage 15 on which an eddy current range finder 14 is mounted. The positions of the stages 12 and 15 are measured with respect to a reference surface 10. A Q value is produced from the results of the above measurement. However, this kind of device is bulky and difficult to operate for the following reasons. The distances between the reference surface 10 and the stages 12 and 15 to be measured are several ten times as great as the Q value. In addition, the stages 12 and 15 which are movable must be positioned and provided with parallelism within the allowable error range of Q value measurement (less than 50 microns inclusive). Moreover, the accuracy of the device is difficult to maintain when the device is included in a production line.

Figure 4A:
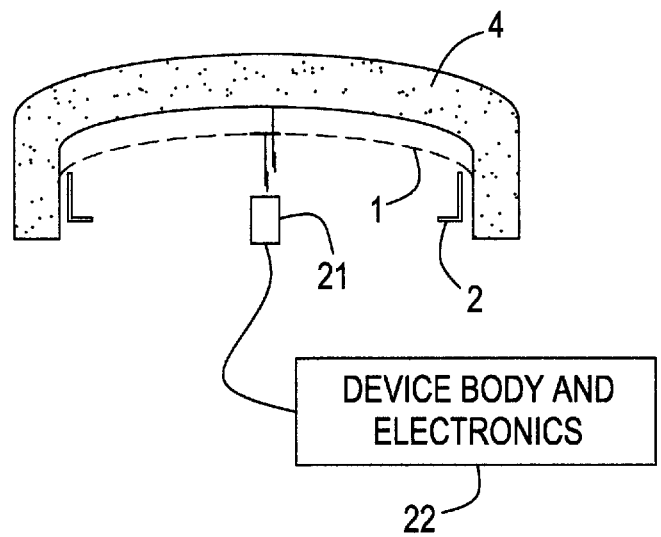
FIG. 4A shows how a measuring device embodying the present invention measures the distance.
Figure 4B:
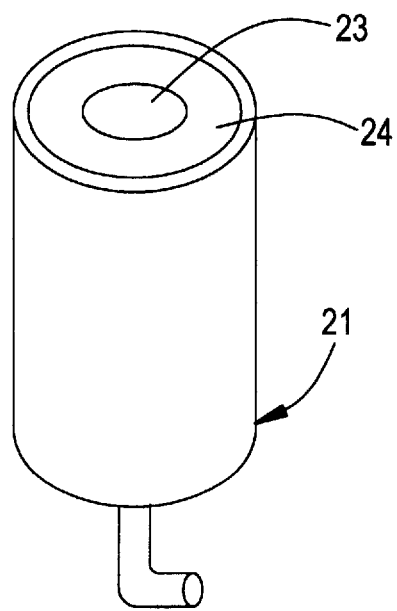
FIG. 4B is an external perspective view of the embodiment.

Referring to FIG. 4A, a device for measuring the distance between a panel and a shadow mask or Q value and embodying the present invention will be described. There are shown in FIG. 4A a shadow mask 1, a frame 2, a panel 4, a range finder 21, and a device body 22 connected to the range finger 21. The device body 22 of the range finder includes a drive section, a computing section, and a display section. As shown in FIG. 4B, the transducer 21 has an ultrasonic wave emitter 23 at its center, and an ultrasonic wave receiver 24 surrounding the emitter 23.

In operation, the transducer 21 is positioned in the vicinity of the inner surface of the shadow mask 1 and oriented such that the emitter 23 emits an ultrasonic wave perpendicularly to the inner surface of the panel 4. In this condition, the drive section of the device body 22 sends a signal to the transducer 21 for causing the emitter 23 to emit an ultrasonic wave in the form of a pulse. Generally, a color CRT mainly used as a terminal unit of a computer has a Q value ranging from about 4 mm to about 10 mm, although it depends on the type and aperture pitch of the shadow mask 1. Let the Q value be 6.8 mm in the following description by way of example.

Figure 5:
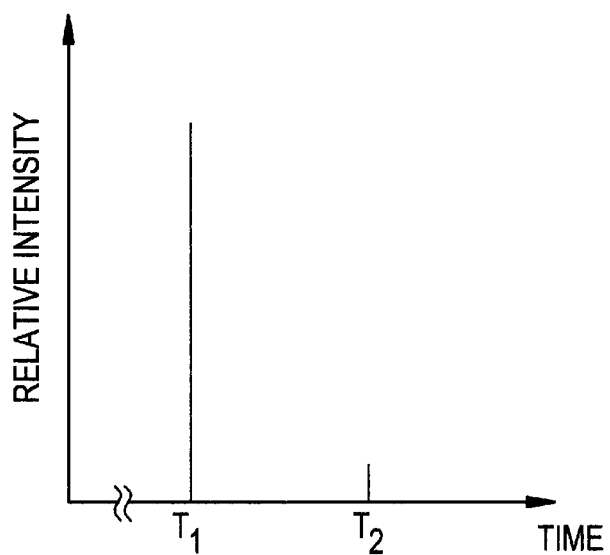
FIG. 5 is a graph showing a relation between times when a first and a second reflection derived from an ultrasonic pulse and the relative intensities of received waves available with to the embodiment.

The ultrasonic wave issuing from the emitter 23 is reflected by the inner surface of the shadow mask 1. The reflection or first reflection from the shadow mask 1 reaches the ultrasonic receiver 24 at a time T1. Subsequently, the wave passed through the aperture of the shadow mask 1 and then reflected by the inner surface of the panel 4 is again passed through the aperture. This reflection or second reflection from the inner surface of the panel 4 arrives at the ultrasonic receiver 24 at a time T2. FIG. 5 is a graph showing a relation between the times T1 and T2 and the relative intensities of the pulses received by the receiver 24.

The sonic speed is 340 mm per second. Because the second reflection travels a distance greater than the distance of travel of the first reflection by twice the Q value, the difference between the times T1 and T2 ($\Delta$=T2−T1) is produced by:

$$\Delta T = 6.8*2/(340*1,000) = 40 \text{ microseconds}$$

The time T2 is therefore 40 microseconds longer than the time T1. It follows that by measuring the time lag $\Delta T$, it is possible to determine the Q value with simple computation. The determined Q value appears on the display, not shown, included in the device body 22.

Because the Q value needs accuracy of 50 microns, the ultrasonic wave needs a single wavelength of 50 microns or below. Therefore, the ultrasonic wave must have an oscillation frequency F of 6.8 MHz or above, as produced by:

$$F = 340*1,000/0.05 = 6.8 \text{ MHz}$$

The shadow mask 1 has an aperture ratio of about 16% to about 18%. Therefore, 84% to 82% of the ultrasonic wave emitted from the emitter 23 as a substantially parallel wave is reflected by the shadow mask 1 while 16% to 18% is passed through the aperture of the shadow mask 1. The wave passed through the aperture is reflected by the inner surface of the panel 4 and reflected thereby. A part of this reflection from the panel 4 is again passed through the aperture of the shadow mask and returned to the range finder 21. However, because the ultrasonic wave spreads in air and because the emitter 23 and receiver 24 are different in position, the relative intensity of the second reflection is usually one-tenth or less of the relative intensity of the first reflection, as shown in FIG. 5, although depending on the position of the range finder 21. It follows that the first and second reflections can be clearly distinguished on the basis of the relative intensity. The receiver 24 is provided with sensitivity high enough to sufficiently catch the second reflection.

As stated above, with the illustrative embodiment, it is possible to measure Q values even smaller than 5 mm without resorting to the removal of the shadow mask 1 from the panel or causing the device to contact the shadow mask 1. In addition, a single transducer 21 suffices the measurement and implements an accurate and easy-to-operate construction.

Figure 6:
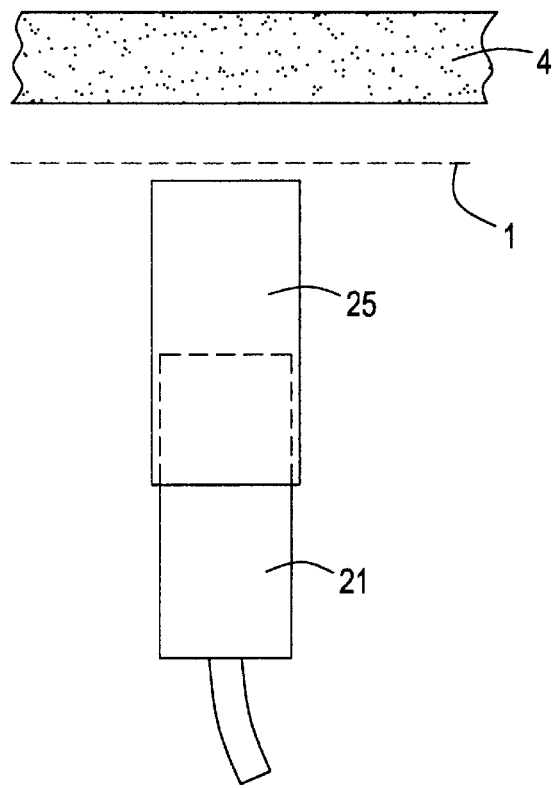
FIG. 6 shows an alternative embodiment of the present invention.

FIG. 6 shows an alternative embodiment of the present invention. As shown, a metallic sleeve 25 is slidably mounted on the front end of the transducer 21. The sleeve 25 is slid to a position close to, but not contacting, the shadow mask 1. With this configuration, the device reduces a loss due to the spread of the ultrasonic wave in air and allows the range finder 21 to be located at a position where it is highly sensitive to the second reflection.

In summary, it will be seen that the present invention provides a device capable of measuring a distance between a panel and a shadow mask, i.e., a Q value without resorting to the removal of the mask, and capable of measuring Q values even smaller than 5 mm without contacting the mask. In addition, the device of the present invention is easy to handle and small size.

Various modifications will become possible for those skilled in the art after receiving the teachings of the present disclosure without departing from the scope thereof.

What is claimed is:

1. A range finder device for measuring a distance between an inner surface of a panel and an inner surface of a shadow mask mounted inside of said panel, said range finder device comprising:

exclusively, a single transducer positioned inside of both said panel and said shadow mask and spaced therefrom, and oriented such that a portion of a pulse emitted by said transducer is reflected back thereunto by the inner surface of said shadow mask, while another portion of said pulse passes through an aperture of said shadow mask and is reflected back onto said transducer by the inner surface of said panel, and means for processing signals corresponding to the reflected pulses to determine said distance.

2. A device as claimed in claim 1, wherein said transducer comprises an ultrasonic wave emitter and an ultrasonic wave receiver.

3. A device as claimed in claim 2, wherein the distance between the inner surface of said panel and the inner surface of said shadow mask is measured on the basis of a time differential between a time when an ultrasonic pulse is emitted from said ultrasonic wave emitter and then reflected from the inner surface of said shadow mask is received by said ultrasonic wave receivers, and a time when said ultrasonic pulse emitted, then passed through an aperture of said shadow mask, then reflected by the inner surface of said panel, and again passed through said aperture is received by said ultrasonic wave receiver.

4. A range finder device for measuring the distance between the inner surface of a color cathode ray tube faceplate panel and the inner surface of a shadow mask, said range finder comprising:

transmitting means for generating an ultrasonic pulse at a frequency and signal strength such that said pulse penetrates shadow mask apertures, reflects off the inner surface of the faceplate panel, and reflects directly off the inner surface of the shadow mask;

receiving means having sufficient gain for measuring reflected ultrasonic pulses of varying return strength, and means for processing signals corresponding to measured time intervals between transmission of ultrasonic pulses and receipt of reflected ultrasonic pulses in order to calculate distance, wherein the transmitting means and receiving means are embodied in a single, unitary component.

5. A device as claimed in claim 4, wherein said transmitting and receiving means comprises, exclusively, a single ultrasonic transducer, wherein the transducer is oriented such that a portion of the pulse emitted by said transducer is reflected back by the inner surface of the shadow mask onto the transducer, and another portion of the emitted pulse passes through the shadow mask apertures, is reflected by the inner surface of the faceplate panel, and passes again through the shadow mask apertures onto the transducer.

6. A device as claimed in claim 5, wherein the distance between the shadow mask and the faceplate panel is calculated on the basis of the time difference between the receipt of two ultrasonic returns captured by the transducer, one return due to reflection caused by the surface of the shadow mask, and the other return due to reflection caused by the surface of the faceplate panel, and both returns result from a single pulse from said transducer.

\* \* \* \* \*